United States Patent
Hirota et al.

(10) Patent No.: US 11,264,772 B2
(45) Date of Patent: Mar. 1, 2022

(54) PHOTOACOUSTIC MEASUREMENT APPARATUS

(71) Applicant: FUJIFILM Corporation, Tokyo (JP)

(72) Inventors: Kazuhiro Hirota, Kanagawa (JP); Katsuaki Kamoike, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 162 days.

(21) Appl. No.: 16/698,157

(22) Filed: Nov. 27, 2019

(65) Prior Publication Data

US 2020/0099191 A1    Mar. 26, 2020

Related U.S. Application Data

(63) Continuation of application No. PCT/JP2018/017338, filed on Apr. 27, 2018.

(30) Foreign Application Priority Data

May 31, 2017  (JP) .............................. JP2017-108677

(51) Int. Cl.
  *H01S 3/00*  (2006.01)
  *H01S 3/067*  (2006.01)
  (Continued)

(52) U.S. Cl.
  CPC ...... *H01S 3/06741* (2013.01); *G01N 29/2418* (2013.01); *H01S 3/1003* (2013.01)

(58) Field of Classification Search
  None
  See application file for complete search history.

(56) References Cited

U.S. PATENT DOCUMENTS

2015/0005612 A1* 1/2015 Suzuki ............... H01S 3/092
                                                    600/407
2015/0045778 A1    2/2015 Ichihara

FOREIGN PATENT DOCUMENTS

JP    63-115390 A    5/1988
JP    2015-29086 A   2/2015
(Continued)

OTHER PUBLICATIONS

International Preliminary Report on Patentability and English translation of the Written Opinion of the International Searching Authority (Forms PCT/IB/326, PCT/IB/373, and PCT/ISA/237) for International Application No. PCT/JP2018/017338, dated Dec. 12, 2019.
(Continued)

*Primary Examiner* — Mark Hellner
(74) *Attorney, Agent, or Firm* — Birch, Stewart, Kolasch & Birch, LLP

(57) ABSTRACT

There is provided a photoacoustic measurement apparatus including a laser light source unit that has a flash lamp for emitting excitation light and a laser rod for emitting laser light in response to incidence of the excitation light, an excitation light source power supply unit that has a capacitor bank for supplying a voltage to the flash lamp, an IGBT for controlling an output of the voltage charged in the capacitor bank to the flash lamp, a discharge control circuit for generating a driving pulse for driving the IGBT, and a pulse width limiting circuit for limiting a pulse width of the driving pulse output from the discharge control circuit, the pulse width limiting circuit being formed of a passive element, and a photoacoustic wave detection unit that detects photoacoustic waves generated inside a subject by emission of light emitted from the laser light source unit to the subject.

6 Claims, 4 Drawing Sheets

(51) Int. Cl.
*H01S 3/10* (2006.01)
*G01N 29/24* (2006.01)

(56) References Cited

FOREIGN PATENT DOCUMENTS

JP         2015-32766 A     2/2015
WO    WO2013129105 A1 *  9/2013  ............. H01S 3/102

OTHER PUBLICATIONS

International Search Report (Form PCT/ISA/210) for International Application No. PCT/JP2018/017338, dated Jun. 12, 2018, with English translation.

* cited by examiner

PHOTOACOUSTIC MEASUREMENT APPARATUS

CROSS-REFERENCE TO RELATED APPLICATIONS

This application is a continuation application of International Application No. PCT/JP2018/017338, filed Apr. 27, 2018, the disclosure of which is incorporated herein by reference in its entirety. Further, this application claims priority from Japanese Patent Application No. 2017-108677, filed May 31, 2017, the disclosure of which is incorporated herein by reference in its entirety.

BACKGROUND OF THE INVENTION

1. Field of the Invention

The present invention relates to a photoacoustic measurement apparatus comprising a laser light source that emits laser light in response to incidence of excitation light emitted from an excitation light source and in particular, relates to an excitation light source power supply unit that supplies a voltage to an excitation light source.

2. Description of the Related Art

As a kind of image examination method capable of examining the state of the inside of the living body in a non-invasive manner, an ultrasound examination method is known. In ultrasound examination, an ultrasound probe capable of transmitting and receiving ultrasound waves is used. In a case where ultrasound waves are transmitted to a subject (living body) from the ultrasound probe, the ultrasound waves propagate through the living body and are reflected on the tissue interface. By receiving the reflected ultrasound waves using the ultrasound probe and calculating the distance based on the time it takes for the reflected ultrasound waves to return to the ultrasound probe, it is possible to image the state of the inside.

In addition, photoacoustic imaging for imaging the inside of the living body using the photoacoustic effect is known. In general, in the photoacoustic imaging, pulsed laser light, such as a laser pulse, is emitted into the living body. In the living body, the living body tissue absorbs the energy of the pulsed laser light, and ultrasound waves (photoacoustic signal) are generated by adiabatic expansion due to the energy. By detecting the photoacoustic signal using an ultrasound probe or the like and forming a photoacoustic image based on the detected signal, it is possible to visualize the inside of the living body based on the photoacoustic signal.

For measurement of photoacoustic waves, it is necessary to emit pulsed laser light with high intensity in many cases. As a light source, a solid state laser device that emits pulsed laser light as a giant pulse by performing Q switch pulse oscillation is used in many cases. The laser light source has a laser rod and a flash lamp for exciting the laser rod.

The flash lamp of the laser light source is driven by a high voltage. However, as a power supply unit for supplying such a high voltage to the flash lamp, for example, JP1988-115390A (JP-S63-115390A) has proposed a power supply unit that supplies a charge voltage charged in a capacitor to a flash lamp. In the power supply unit disclosed in JP1988-115390A (JP-S63-115390A), a thyristor is provided between the capacitor and the flash lamp, and a voltage is supplied from the capacitor to the flash lamp by switching using the thyristor. The thyristor is switched between a conduction state and a non-conduction state based on a pulse signal generated in a pulse generation circuit.

Here, the intensity of the pulsed laser light output from the laser light source is proportional to the lighting time of the flash lamp. Since the pulsed laser light is emitted to the living body, it is necessary to set an upper limit value of the intensity for ensuring the safety of the living body. That is, it is necessary to set an upper limit value for the lighting time of the flash lamp.

JP1988-115390A (JP-S63-115390A) has proposed to provide a pulse width limiting circuit as a protection circuit to limit the lighting time of the flash lamp. The pulse width limiting circuit disclosed in JP1988-115390A (JP-S63-H5390A) outputs a signal to a discharge stop circuit such that the lighting time of the flash lamp does not exceed an upper limit value set in advance. The discharge stop circuit stops the output of the pulse signal from the pulse generation circuit based on the input signal.

SUMMARY OF THE INVENTION

Here, in the configuration disclosed in JP1988-115390A (JP-563-H5390A), in a case where the pulse generation circuit or the pulse width limiting circuit fails, the thyristor continues to be in a conduction state. In this case, there is a problem that excessive laser light is output. In addition, in a case where the pulse generation circuit and the pulse width limiting circuit are configured by a logic circuit such as an integrated circuit (IC) as disclosed in JP1988-115390A (JP-S63-115390A). there is a problem that failure is easily caused by the influence of static electricity and the like. Even in a case where these circuits do not fail, there is also a concern that the pulse signal continues to be output to the thyristor due to a malfunction caused by electromagnetic compatibility (EMC).

In view of the above circumstances, an object of the present invention is to provide a photoacoustic measurement apparatus capable of preventing output of the excessive laser light from the laser light source.

A photoacoustic measurement apparatus of the embodiment of the present invention comprises a laser light source that has an excitation light source, which emits excitation light, and a laser medium, which emits laser light in response to incidence of the excitation light emitted from the excitation light source; an excitation light source power supply unit that has a capacitor for supplying a charged voltage to the excitation light source, a switch circuit for controlling an output of the voltage charged in the capacitor to the excitation light source, a discharge control circuit for generating a driving pulse which drives the switch circuit, and a pulse width limiting circuit for limiting a pulse width of the driving pulse output from the discharge control circuit, the pulse width limiting circuit being formed of a passive element; and a photoacoustic wave detection unit that detects photoacoustic waves generated inside a subject by emission of light emitted from the laser light source to the subject.

In the photoacoustic measurement apparatus of the embodiment of the present invention, it is preferable that the passive element is a pulse transformer.

In the photoacoustic measurement apparatus of the embodiment of the present invention, the pulse width limiting circuit may limit the pulse width of the driving pulse to be equal to or less than a time obtained by dividing an ET product of the pulse transformer by a voltage value of the driving pulse.

In the photoacoustic measurement apparatus of the embodiment of the present invention, the discharge control circuit may include a pulse width setting circuit for outputting a pulse signal having a pulse width set in advance and a pulse width control circuit for generating the driving pulse by limiting the pulse width of the pulse signal output from the pulse width setting circuit to be equal to or less than an upper limit pulse width set in advance.

In the photoacoustic measurement apparatus of the embodiment of the present invention, it is preferable that the discharge control circuit has the logic circuit.

In the photoacoustic measurement apparatus of the embodiment of the present invention, it is preferable that the pulse width control circuit is configured to change the upper limit pulse width.

In the photoacoustic measurement apparatus of the embodiment of the present invention, it is preferable that the capacitor is a capacitor bank.

According to the photoacoustic measurement apparatus of the embodiment of the present invention, there are provided a laser light source having an excitation light source and a laser medium, an excitation light source power supply unit that has a capacitor for supplying a voltage to the excitation light source, a switch circuit for controlling an output of the voltage charged in the capacitor to the excitation light source, a discharge control circuit for generating a driving pulse which drives the switch circuit, and a pulse width limiting circuit for limiting a pulse width of the driving pulse output from the discharge control circuit, the pulse width limiting circuit being formed of a passive element.

According to the photoacoustic measurement apparatus of the embodiment of the present invention, since the pulse width limiting circuit is formed of a passive element in this way, it is possible to prevent the output of the excessive laser light from the laser light source.

DESCRIPTION OF THE PREFERRED EMBODIMENTS

Figure 1:
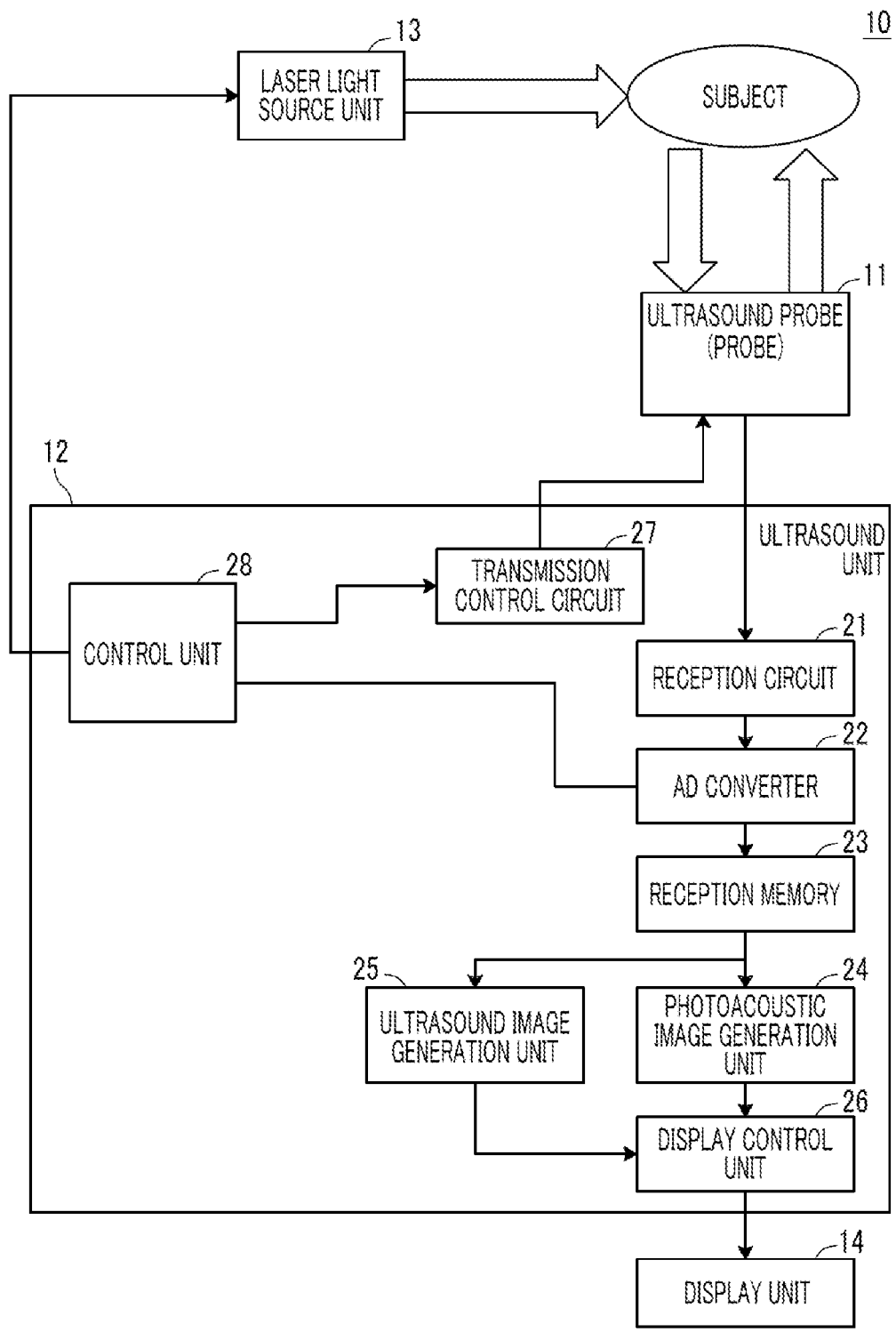
FIG. 1 is a diagram showing a schematic configuration of a photoacoustic image generation apparatus using an embodiment of a photoacoustic measurement apparatus of the embodiment of the present invention.

Hereinafter, a photoacoustic image generation apparatus using an embodiment of a photoacoustic measurement apparatus of the embodiment of the present invention will be described in detail with reference to the diagrams. FIG. 1 is a diagram showing a schematic configuration of a photoacoustic image generation apparatus 10 of the present embodiment. The photoacoustic image generation apparatus 10 of the present embodiment is characterized by the configuration of an excitation light source power supply unit 59 of a laser light source unit 13. First, the overall configuration of the photoacoustic image generation apparatus 10 will be described.

The photoacoustic image generation apparatus 10 comprises an ultrasound probe (probe) 11, an ultrasound unit 12, a laser light source unit 13, and a display unit 14. In the present embodiment, an ultrasound wave is used as an acoustic wave. However, the present invention is not limited to the ultrasound wave, and an acoustic wave having an audible frequency may be used as long as an appropriate frequency can be selected according to an examination target, measurement conditions, or the like.

The laser light source unit 13 has, for example, a solid state laser light source that emits laser light, and emits laser light as measurement light that is to be emitted to a subject. The laser light source unit 13 of the present embodiment is configured to receive a trigger signal from a control unit 28 of the ultrasound unit 12 and output pulsed laser light. In the present embodiment, an alexandrite laser light source using a Q switch is used as the laser light source unit 13.

The pulsed laser light emitted from the laser light source unit 13 is guided to an ultrasound probe 11 by using, for example, light guiding means such as an optical fiber, and is emitted from the ultrasound probe 11 to the subject. The emission position of the pulsed laser light is not particularly limited, and the pulsed laser light may be emitted from a place other than the ultrasound probe 11.

Within the subject, photoacoustic waves are generated due to a light absorber absorbing the energy of the emitted pulsed laser light. The ultrasound probe 11 has a plurality of ultrasound transducers arranged in a one-dimensional manner or in a two-dimensional manner, for example. The ultrasound probe 11 detects photoacoustic waves from the inside of the subject with the plurality of ultrasound transducers and outputs a photoacoustic wave signal. The ultrasound probe 11 transmits ultrasound waves to the subject, detects reflected ultrasound waves from the subject with respect to the transmitted ultrasound waves, and outputs a reflected wave signal. As the ultrasound probe 11, a linear ultrasound probe, a convex ultrasound probe, a sector ultrasound probe, or the like can be used. In the present embodiment, the ultrasound probe 11 corresponds to a photoacoustic wave detection unit of the present invention. The specific configuration of the laser light source unit 13 will be described in detail later.

The ultrasound unit 12 has a reception circuit 21, an analog to digital converter (AD converter) 22, a reception memory 23, a photoacoustic image generation unit 24, an ultrasound image generation unit 25, a display control unit 26, a transmission control circuit 27, and the control unit 28.

The ultrasound unit 12 is configured to include, for example, a computer, and typically has a processor, a memory, a bus, and the like. Programs relevant to photoacoustic image generation and ultrasound image generation are installed on the memory of the ultrasound unit 12. By running the programs using the control unit 28 configured by a processor, functions of the photoacoustic image generation unit 24, the ultrasound image generation unit 25, and the display control unit 26 are realized. That is, each of these units is formed by the memory on which the programs are installed and the processor.

In the present embodiment, each unit is caused to function by executing the programs by the processor. However, the present invention is not limited thereto, and a part or all of the functions may be realized by the hardware. The configuration of the hardware is not particularly limited, and can be realized by appropriately combining a plurality of integrated circuits (ICs), application specific integrated circuits (ASICs), field-programmable gate arrays (FPGAs), memories, circuits formed of discrete components, and the like.

The reception circuit 21 receives the photoacoustic wave signal and the reflected wave signal output from the ultrasound probe 11. Typically, the reception circuit 21 includes a low noise amplifier, a variable gain amplifier, and a low pass filter. The photoacoustic wave signal and the reflected wave signal output from the ultrasound probe 11 are amplified by the low noise amplifier, and then the gain is adjusted according to the depth by the variable gain amplifier and high-frequency components are cut by the low pass filter.

The AD converter 22 converts the photoacoustic wave signal and the reflected wave signal received by the reception circuit 21 into digital signals. The AD converter 22 samples the photoacoustic wave signal and the reflected wave signal at predetermined sampling periods based on, for example, a sampling clock signal having a predetermined period. The AD converter 22 stores the sampled photoacoustic wave signal and reflected wave signal (sampling data) in the reception memory 23. The reception circuit 21 and the AD converter 22 may be formed as, for example, one IC, or may be formed as individual ICs.

The photoacoustic image generation unit 24 generates a photoacoustic image based on the photoacoustic wave signal stored in the reception memory 23. The generation of a photoacoustic image includes, for example, image reconstruction such as a Fourier transfer algorithm (FTA) method or a delayed addition (phase matching addition) method, detection, and logarithmic conversion.

The ultrasound image generation unit 25 generates an ultrasound image based on the reflected wave signal stored in the reception memory 23. The generation of an ultrasound image also includes image reconstruction such as phase matching addition, detection, and logarithmic conversion.

The control unit 28 controls each unit of the photoacoustic image generation apparatus 10, and comprises a trigger control circuit (not shown) in the present embodiment. The trigger control circuit transmits a laser trigger signal to the laser light source unit 13, for example, at the start of the photoacoustic image generation apparatus 10. Therefore, in the laser light source unit 13, a flash lamp 52 to be described is lit to start the excitation of a laser rod 51. Then, the excitation state of the laser rod 51 is maintained, so that the laser light source unit 13 can output pulsed laser light.

Also, in a case of generating a photoacoustic image, the control unit 28 transmits a Qsw trigger signal from the trigger control circuit to the laser light source unit 13. That is, the control unit 28 controls the output timing of the pulsed laser light from the laser light source unit 13 using the Qsw trigger signal. In the present embodiment, the control unit 28 transmits a sampling trigger signal to the AD converter 22 simultaneously with the transmission of the Qsw trigger signal. The sampling trigger signal is a signal of the start timing of the sampling of the photoacoustic wave signal in the AD converter 22. Thus, it is possible to sample the photoacoustic wave signal in synchronization with the output of laser light by using the sampling trigger signal.

In a case of generating an ultrasound image, the control unit 28 transmits an ultrasound wave transmission trigger signal for instructing the transmission control circuit 27 to transmit ultrasound waves. In a case where the trigger signal is received, the transmission control circuit 27 causes the ultrasound probe 11 to transmit ultrasound waves. After the transmission of ultrasound waves, the ultrasound probe 11 detects reflected ultrasound waves from the subject and outputs a reflected wave signal.

The reflected wave signal output from the ultrasound probe 11 is input to the AD converter 22 through the reception circuit 21. The control unit 28 transmits a sampling trigger signal to the AD converter 22 according to the timing of ultrasound wave transmission, thereby starting the sampling of the reflected wave signal.

The control unit 28 controls each unit so that the photoacoustic image and the ultrasound image are acquired at the same timing, for example. The same timing referred to herein does not mean completely the same timing but means that the photoacoustic image and the ultrasound image are sequentially acquired within a short time of a predetermined timing. That is, the photoacoustic image and the ultrasound image are sequentially acquired at the same frame rate.

For example, the display control unit 26 displays the photoacoustic image and the ultrasound image separately on the display unit 14, or displays a composite image of the photoacoustic image and the ultrasound image on the display unit 14. The display control unit 26 performs image composition by superimposing the photoacoustic image and the ultrasound image, for example.

Figure 2:
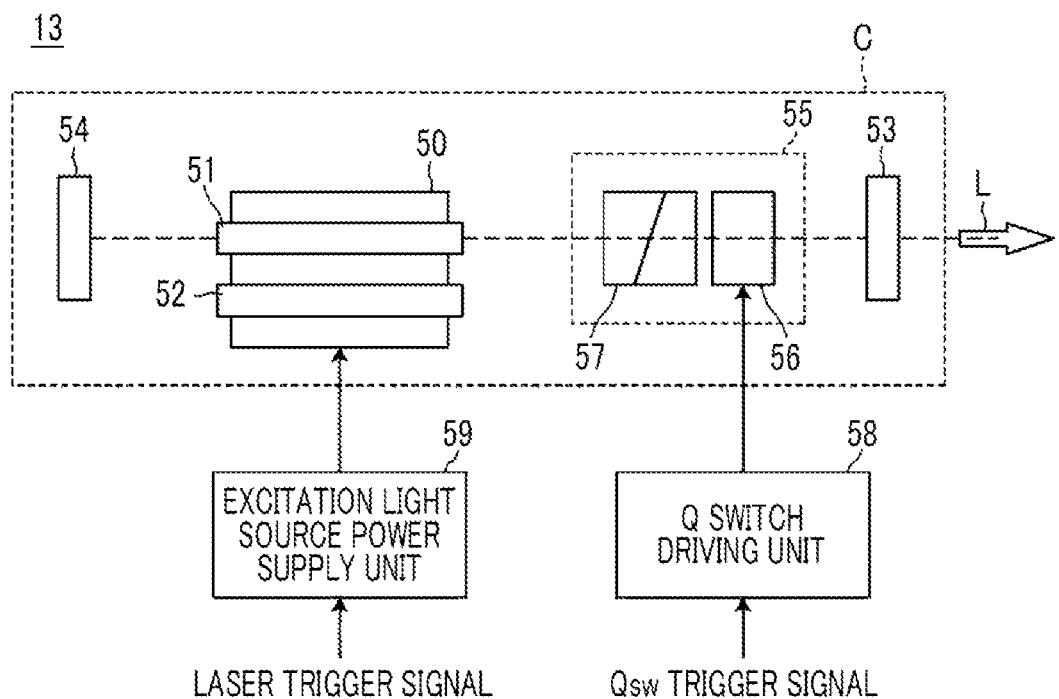
FIG. 2 is a diagram showing a specific configuration of a laser light source unit.

Next, the specific configuration of the above laser light source unit 13 will be described. FIG. 2 is a diagram showing the specific configuration of the laser light source unit 13.

As shown in FIG. 2, the laser light source unit 13 of the present embodiment comprises the laser rod 51, the flash lamp 52, a laser chamber 50, a first mirror 53, a second mirror 54, a Q value changing unit 55, a Q switch driving unit 58, and an excitation light source power supply unit 59. In the present embodiment, a laser light source of the present invention is formed by the laser rod 51, the flash lamp 52, the laser chamber 50, the first mirror 53, the second mirror 54, and the Q value changing unit 55.

The flash lamp 52 emits excitation light. The flash lamp 52 is intermittently driven by the high voltage output from the excitation light source power supply unit 59, and emits pulsed excitation light. The flash lamp 52 corresponds to an excitation light source of the present invention. The excitation light source is not limited to the flash lamp 52, and other excitation light sources may be used.

The laser rod 51 is a bar-shaped laser medium, and receives the excitation light emitted from the flash lamp 52 and emits laser light. As the laser rod 51, for example, alexandrite crystal can be used, but other known laser mediums, such as Nd: YAG crystal, can be used without being limited thereto. In the present embodiment, the laser rod 51 corresponds to a laser medium of the present invention.

The laser rod 51 and the flash lamp 52 are housed in the laser chamber 50. A reflection surface is provided inside the laser chamber 50, and the light emitted from the flash lamp 52 is directly emitted to the laser rod 51 or is reflected on the reflection surface and emitted to the laser rod 51. The inside of the laser chamber 50 may be a diffuse reflection surface.

The first mirror 53 and the second mirror 54 are arranged along the optical axis of the laser rod 51. The first mirror 53 and the second mirror 54 are arranged so as to face each other with the laser rod 51 interposed therebetween. The laser light emitted from the laser rod 51 is reflected by the first mirror 53 and the second mirror 54 and reciprocates between the first mirror 53 and the second mirror 54. That is, a resonator C is formed by the first mirror 53 and the second mirror 54. The first mirror 53 is an output coupler (OC). Then, by the control of the Q value of the resonator C by the Q value changing unit 55, pulsed laser light L emitted from the first mirror 53.

In the present embodiment, the first mirror 53 and the second mirror 54 are arranged along the optical axis of the laser rod 51 to form the optical path of the resonator C in a linear shape. However, the present invention is not limited thereto, and a prism or the like may be provided on the optical path between the first mirror 53 and the second mirror 54 to bend the optical axis.

The Q value changing unit 55 is inserted in the optical path of the resonator C to change the Q value of the resonator. In the present embodiment, the Q value changing unit 55 is disposed between the first mirror 53 and the laser rod 51. However, the Q value changing unit 55 may be disposed between the laser rod 51 and the second mirror 54 without being limited thereto. The Q value changing unit 55 comprises a Q switch 56 and a polarizer 57.

The Q switch 56 changes the Q value of the resonator C by changing the polarization state of light transmitted therethrough according to the applied voltage. As the Q switch 56, it is possible to use an electro-optical element that changes the polarization state of light transmitted therethrough according to the applied voltage. For example, a Pockels cell can be used as the Q switch 56.

The Q switch 56 changes the state of the resonator C to a low Q state in a case where a first voltage corresponding to Q switch OFF is applied. The low Q state is a state in which the Q value of the resonator C is lower than a laser oscillation threshold value. The Q switch OFF refers to the state of the Q switch 56 that changes the state of the resonator C to the low Q state as described above. The Q switch 56 of the present embodiment functions as a quarter wavelength plate in a case where the first voltage is applied.

The Q switch 56 changes the state of the resonator C to a high Q state in a case where a second voltage corresponding to Q switch ON is applied. The high Q state is a state in which the Q value of the resonator C is higher than the laser oscillation threshold value. The Q switch ON refers to the state of the Q switch 56 that changes the state of the resonator C to the high Q state as described above. The Q switch 56 of the present embodiment does not change the polarization state of light transmitted therethrough in a case where the second voltage is applied.

The relationship between the first voltage and the second voltage is that the absolute value of the first voltage is larger than the absolute value of the second voltage. The voltage may be a positive voltage or a negative voltage. The second voltage can be set to, for example, 0 V (no voltage applied).

The polarizer 57 is disposed between the laser rod 51 and the Q switch 56. The polarizer 57 allows only linearly polarized light in a predetermined direction to pass therethrough. As the polarizer 57, for example, a beam splitter that transmits linearly polarized light in a predetermined direction and reflects linearly polarized light in a direction perpendicular to the predetermined direction can be used. In the present embodiment, a beam splitter that transmits p-polarized light and reflects s-polarized light is used as the polarizer 57. The polarizer 57 may be omitted in a case where the laser rod 51 itself has polarized light selectivity, such as a case where alexandrite crystal is used as the laser rod 51.

Specifically, in a case where the first voltage is applied to the Q switch 56, the Q switch 56 functions as a quarter wavelength plate as described above. First, p-polarized light incident on the polarizer 57 from the laser rod 51 passes through the polarizer 57, and becomes circularly polarized light in a case of passing through the Q switch 56. Then, the circularly polarized light transmitted through the Q switch 56 is reflected by the first mirror 53 and is then incident on the Q switch 56 again from the opposite direction. The circularly polarized light incident on the Q switch 56 in the opposite direction becomes linearly polarized light again in a case of passing through the Q switch 56, but is incident on the polarizer 57 as s-polarized light rotated by 90° and is emitted to the outside of the optical path of the resonator C. Accordingly, laser oscillation does not occur in the laser rod 51.

On the other hand, in a case where the voltage applied to the Q switch 56 is the second voltage (0 V), the p-polarized light incident on the polarizer 57 from the laser rod 51 passes through the Q switch 56 without changing the polarization state and is reflected by the first mirror 53. The light reflected by the first mirror 53 also passes through the Q switch 56 without changing the polarization state, further passes through the polarizer 57, and returns to the laser rod 51. In this manner, laser oscillation occurs.

As described above, in a case where the first voltage is applied to the Q switch 56, the Q switch 56 is made to function as a quarter wavelength plate, so that the laser light emitted from the laser rod 51 is emitted to the outside of the optical path of the resonator C and as a result, the resonator C can be changed to the low Q state. On the other hand, in a case where the second voltage is applied to the Q switch 56, the Q switch 56 is not made to function as a quarter wavelength plate, so that the incident laser light passes through the Q switch 56 as it is and as a result, the resonator C can be changed to the high Q state.

The Q switch driving unit 58 drives the Q switch 56 by applying the first voltage and the second voltage described above to the Q switch 56. The Q switch driving unit 58 changes a voltage applied to the Q switch 56 based on the Qsw trigger signal output from the control unit 28 of the ultrasound unit 12.

Figure 3:
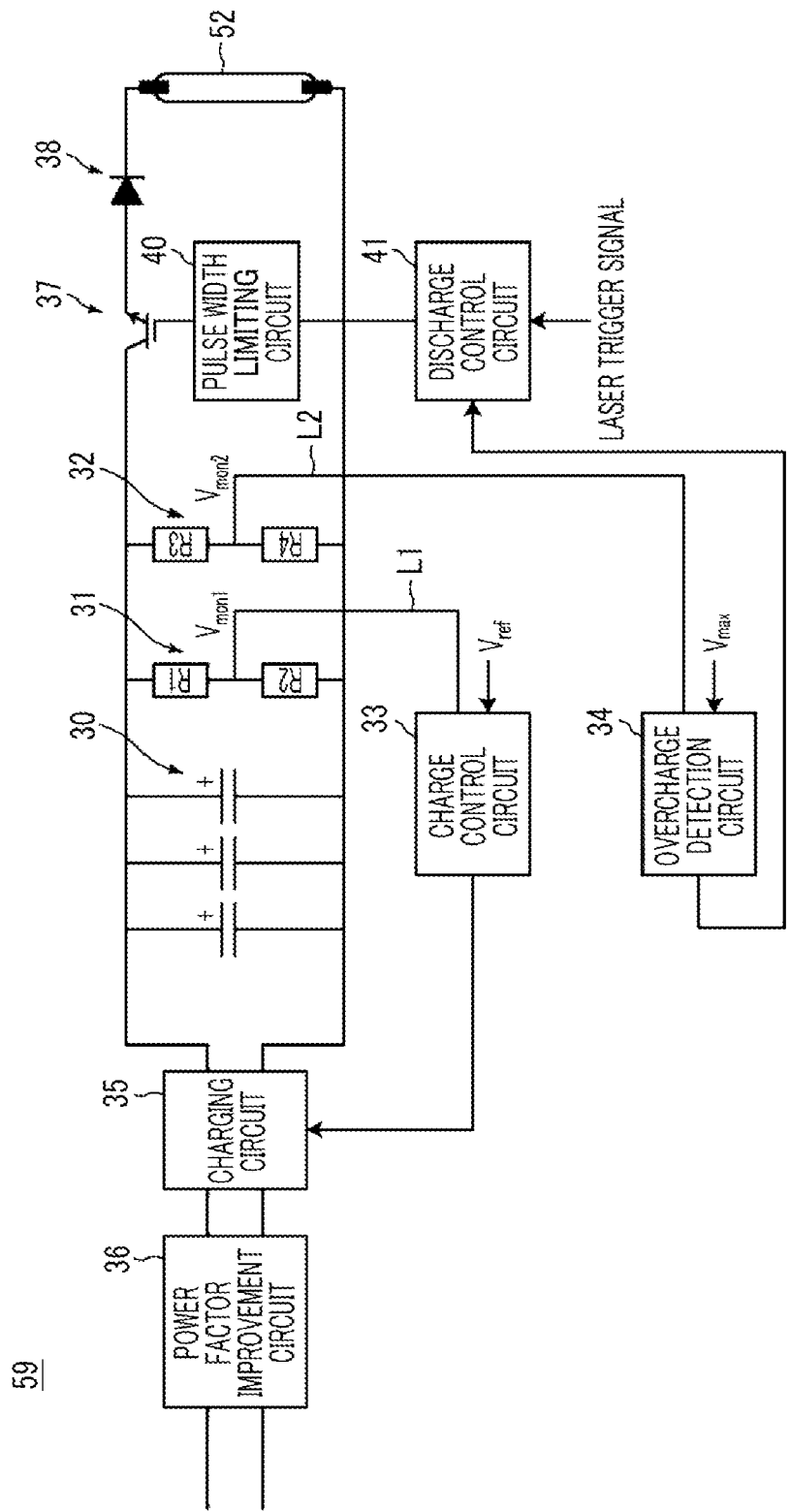
FIG. 3 is a diagram showing a specific configuration of an excitation light source power supply unit.

The excitation light source power supply unit 59 applies a high voltage to the flash lamp 52 according to the laser trigger signal output from the ultrasound unit 12. FIG. 3 is a diagram showing the specific configuration of the excitation light source power supply unit 59. As shown in FIG. 3, the excitation light source power supply unit 59 comprises a capacitor bank 30, a first voltage dividing circuit 31, a second voltage dividing circuit 32, a charge control circuit 33, an overcharge detection circuit 34, a charging circuit 35, a power factor improvement circuit 36, an insulated gate bipolar transistor (IGBT) 37, a diode 38, a pulse width limiting circuit 40, and a discharge control circuit 41.

The capacitor bank 30 supplies a voltage charged by the charging circuit 35 to the flash lamp 52. Based on the voltage supplied from the commercial power supply through the power factor improvement circuit 36, the charging circuit 35 supplies a voltage to the capacitor bank 30 to charge the capacitor bank 30. As the charging circuit 35 and the power factor improvement circuit 36, a general known circuit can be used.

The first voltage dividing circuit 31 is connected in parallel to the capacitor bank 30, and comprises a first resistance element R1 and a second resistance element R2. The first resistance element R1 and the second resistance element R2 are connected in series to each other. Then, a wiring L1 is connected between the first resistance element R1 and the second resistance element R2, and a first divided voltage Vmon1 determined by the resistance value of the first resistance element R1 and the resistance value of the second resistance element R2 is output to the wiring L1. The charge control circuit 33 is connected to the output destination of the wiring L1, and the first divided voltage Vmon1 is supplied to the charge control circuit 33.

The second voltage dividing circuit 32 is connected in parallel to the capacitor bank 30 and the first voltage dividing circuit 31, and comprises a third resistance element R3 and a fourth resistance element R4. The third resistance element R3 and the fourth resistance element R4 are connected in series to each other. Then, a wiring L2 is connected between the third resistance element R3 and the fourth resistance element R4, and a second divided voltage Vmon2 determined by the resistance value of the third resistance element R3 and the resistance value of the fourth resistance element R4 is output to the wiring L2. The charge control circuit 33 is connected to the output destination of the wiring L2, and the second divided voltage Vmon2 is supplied to the charge control circuit 33.

In the present embodiment, it is assumed that the relationship among the resistance value r1 of the first resistance element R1, the resistance value r2 of the second resistance element R2, the resistance value r3 of the third resistance element R3, and the resistance value r4 of the fourth resistance element R4 is r1:r2=r3:r4 and the first divided voltage Vmon1 and the second divided voltage Vmon2 have approximately the same magnitude. However, the relationship is not limited thereto, and r1:r2 and r3:r4 may be different.

In the present embodiment, r1:r2=r3:r1=99:1 is assumed. That is, the resistance value r1 of the first resistance element R1 on the high potential side is larger than the resistance value r2 of the second resistance element R2 on the low potential side, and the resistance value r3 of the third resistance element R3 on the high potential side is larger than the resistance value r4 of the fourth resistance element R4 on the low potential side.

Therefore, for example, in a case where the voltage charged in the capacitor bank 30 is 600 V, the first divided voltage Vmon1 and the second divided voltage Vmon2 are about 6 V. In a case where the charge control circuit 33 to which the first divided voltage Vmon1 is supplied and the overcharge detection circuit 34 to which the second divided voltage Vmon2 is supplied are formed by, for example, an integrated circuit (IC), a general-purpose IC can be used by setting the first divided voltage Vmon1 and the second divided voltage Vmon2 to about 6 V as described above. As a result, it is possible to reduce the cost. However, r1:r2 and r3:r4 are not limited to 99:1, and can be appropriately changed according to the allowable input voltages of the charge control circuit 33 and the overcharge detection circuit 34 that are supply destinations of the first divided voltage Vmon1 and the second divided voltage Vmon2. By setting the values of r1 and r3 to be smaller than 99 and providing an attenuator, an operational amplifier, and the like at a stage before the charge control circuit 33 and the overcharge detection circuit 34, voltages input to the charge control circuit 33 and the overcharge detection circuit 34 may be reduced to the allowable input voltages.

The charge control circuit 33 controls the charged voltage of the capacitor bank 30 by controlling the charging circuit 35. Specifically, the charge control circuit 33 of the present embodiment calculates a difference voltage between the input first divided voltage Vmon1 and the reference voltage Vref set in advance and controls the charging circuit 35 based on the difference voltage, thereby performing control so that the charged voltage of the capacitor bank 30 becomes a voltage value set in advance. That is, the charge control circuit 33 of the present embodiment controls the charged voltage of the capacitor bank 30 so as to be 600 V.

The overcharge detection circuit 34 detects overcharge of the capacitor bank 30. Specifically, based on the input second divided voltage Vmon2 and the maximum voltage Vmax set in advance, the overcharge detection circuit 34 of the present embodiment detects that the charged voltage of the capacitor bank 30 exceeds the maximum voltage Vmax to cause overcharge. Then, in a case where the overcharge of the capacitor bank 30 is detected, the overcharge detection circuit 34 outputs a control signal to the discharge control circuit 41 to stop power supply (discharge) from the capacitor bank 30 to the flash lamp 52. In the present embodiment, the maximum voltage Vmax is set to 600 V.

The IGBT 37 is connected between the capacitor bank 30 and the flash lamp 52. The IGBT 37 is a semiconductor switch circuit, and controls the output of the voltage charged in the capacitor bank 30 to the flash lamp 52. In the present embodiment, the IGBT 37 corresponds to the switch circuit of the present invention. Only while the IGBT 37 is in the ON state, discharge from the capacitor bank 30 to the flash lamp 52 occurs.

Figure 4:
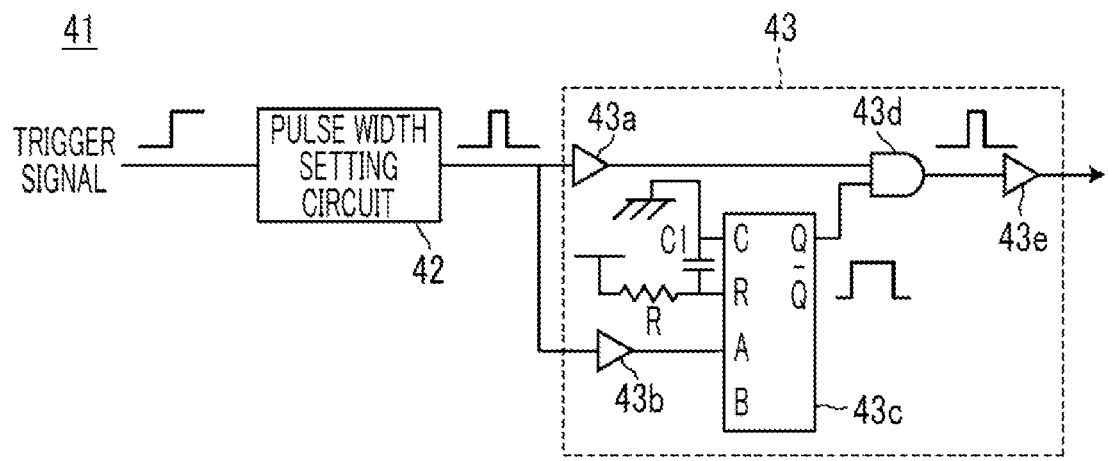
FIG. 4 is a diagram showing a specific configuration of a discharge control circuit.
Figure 5:
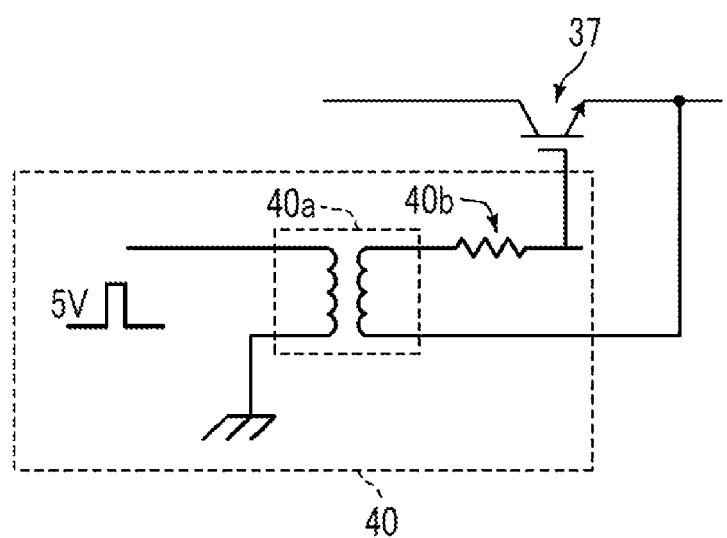
FIG. 5 is a diagram showing a specific configuration of a pulse width limiting circuit.

The discharge control circuit 41 generates a driving pulse for driving the IGBT 37 according to the laser trigger signal output from the ultrasound unit 12. FIG. 4 is a diagram showing a configuration of the discharge control circuit 41. The discharge control circuit 41 comprises a pulse width setting circuit 42 and a pulse width control circuit 43. The pulse width setting circuit 42 generates and outputs a pulse signal having a pulse width set in advance in a case where the laser trigger signal is received.

The pulse width control circuit 43 generates the driving pulse by limiting the pulse width of the pulse signal output from the pulse width setting circuit 42 to be equal to or less than an upper limit pulse width set in advance. Specifically, the pulse width control circuit 43 limits the pulse width such that, in a case where the pulse width of the pulse signal becomes larger than the pulse width set in advance, for example, due to a malfunction of the pulse width setting circuit 42, the pulse width does not exceed the upper limit pulse width set in advance.

The pulse width control circuit 43 is formed of a logic circuit, and comprises a monostable multi-vibrator circuit 43c, an AND circuit 43d, and buffer circuits 43a, 43b, and 43e. The pulse signal output from the pulse width setting circuit 42 is input to the AND circuit 43d via the buffer circuit 43a and also input to the monostable multi-vibrator circuit 43c via the buffer circuit 43b.

The monostable multi-vibrator circuit 43c outputs the input pulse signal as a pulse signal having an upper limit pulse width (for example, 200 µs) set in advance in consideration of safety. The upper limit pulse width is defined by a product of the resistance value of a resistance element R connected to the monostable multi-vibrator circuit 43c and the capacitance of a capacitor C1.

Then, the pulse signal output from the pulse width setting circuit 42 and the pulse signal output from the monostable multi-vibrator circuit 43c are input to the AND circuit 43d. The AND circuit 43d outputs an operation result of an AND of the two input pulse signals as a driving pulse. Therefore, even in a case where the pulse width of the pulse signal output from the pulse width setting circuit 42 exceeds the upper limit pulse width, unless a failure or the like occurs, a driving pulse having a pulse width equal to or higher than the upper limit pulse width for safety is not output from the pulse width control circuit 43 by operating the AND of the pulse signal having the upper limit pulse width output from the monostable multi-vibrator circuit 43c and the pulse signal output from the pulse width setting circuit 42. The driving pulse is output to the pulse width limiting circuit 40 via a buffer circuit 43e.

The pulse width control circuit 43 is not limited to the above configuration, and may be configured by, for example, the field-programmable gate array (FPGA) and the like. In this case, for example, the upper limit pulse width may be configured to be changeable based on a control signal output from the control unit 28 of the ultrasound unit 12.

The pulse width limiting circuit 40 is formed of a passive element, and limits the pulse width of the driving pulse output from the discharge control circuit 41. For example, in a case where the pulse width control circuit 43 formed of a logic circuit fails and a driving pulse having a pulse width exceeding a threshold value set in advance is output from the discharge control circuit 41, the pulse width limiting circuit 40 limits the pulse width of the driving pulse to output the driving pulse as a driving pulse having a pulse width equal to or less than the threshold value.

Specifically, the pulse width limiting circuit 40 of the present embodiment comprises a pulse transformer 40a and a resistance element 40b. The pulse transformer 40a is a passive element that transmits an input driving pulse. The pulse transformer 40a transmits a pulse waveform signal represented by the ET product. For example, in a case where the voltage value of the driving, pulse input to the pulse transformer 40a is 5 V and the ET product of the pulse transformer 40a is 1000 Vμ, the pulse transformer 40a can output only a driving pulse having a pulse width of 200 μs obtained by dividing the ET product by the voltage value of the driving pulse. That is, the pulse transformer 40a limits the pulse width of the input driving pulse to 200 μs. Also, the pulse transformer 40a is not limited to this, and a pulse transformer having a desired ET product according to the voltage value of the driving pulse and the pulse width to be limited can be appropriately selected and used.

Therefore, by limiting the pulse width of the driving pulse by the pulse width limiting circuit 40, even in a case where a driving pulse having a pulse width exceeding an upper limit pulse width set in advance is output from the discharge control circuit 41, for example, due to a failure, the pulse width of the driving pulse can be limited to an appropriate pulse width by the pulse width limiting circuit 40. Since the pulse width limiting circuit 40 is configured separately from the discharge control circuit 41, the pulse width limiting circuit 40 is not easily affected by the failure of the discharge control circuit 41. Moreover, since the pulse width limiting circuit 40 is not formed of a logic circuit unlike the discharge control circuit 41 but is formed of a passive element, it is difficult to fail and does not malfunction by the influence of EMC. Additionally, since the pulse width limiting circuit 40 is less likely to fail by the same cause as that of the discharge control circuit 41, the pulse width of the driving pulse can be more reliably limited.

In the present embodiment, the pulse transformer 40a is used as the pulse width limiting circuit 40, but the present invention is not limited thereto. The pulse width of the driving pulse may be limited by using a filter circuit formed of a passive element such as an inductor and a capacitor.

While the present invention has been described based on the preferred embodiments thereof, the photoacoustic measurement apparatus of the embodiment of the present invention is not limited only to the embodiments described above, and various modifications and changes from the configuration of the above-described embodiments are also included in the scope of the present invention.

EXPLANATION OF REFERENCES

10: photoacoustic image generation apparatus
11: ultrasound probe
12: ultrasound unit
13: laser light source unit
14: display unit
21: reception circuit
22: converter
23: reception memory
24: photoacoustic image generation unit
25: ultrasound image generation unit
26: display control unit
27: transmission control circuit
28: control unit
30: capacitor bank
31: first voltage dividing circuit
32: second voltage dividing circuit
33: charge control circuit
34: overcharge detection circuit
35: charging circuit
36: power factor improvement circuit
38: diode
40: pulse width limiting circuit
40a: pulse transformer
40b: resistance element
41: discharge control circuit
42: pulse width setting circuit
43: pulse width control circuit
43a, 43b, 43e: buffer circuit
43c: flip flop circuit
43d: AND circuit
50: laser chamber
51: laser rod
52: flash lamp
53: first mirror
54: second mirror
55: Q value changing unit
56: Q switch
57: polarizer
58: Q switch driving unit
59: excitation light source power supply unit
C: resonator
L: pulsed laser light
L1: wiring
L2: wiring
R1: resistance element
R2: resistance element
R3: resistance element
R4: resistance element
Vmax: maximum voltage
Vmon1: first divided voltage
Vmon2: second divided voltage
Vref: reference voltage

What is claimed is:

1. A photoacoustic measurement apparatus, comprising:
a laser light source that has an excitation light source, which emits excitation light, and a laser medium, which emits laser light in response to incidence of the excitation light emitted from the excitation light source;
an excitation light source power supply unit that has a capacitor for supplying a charged voltage to the excitation light source, a switch circuit for controlling an output of the voltage charged in the capacitor to the excitation light source, a discharge control circuit for generating a driving pulse which drives the switch circuit, and a pulse width limiting circuit for limiting a pulse width of the driving pulse output from the discharge control circuit, the pulse width limiting circuit being formed of a passive element; and
a photoacoustic wave detection unit that detects photoacoustic waves generated inside a subject by emission of light emitted from the laser light source to the subject, wherein the passive element is a pulse transformer.

2. The photoacoustic measurement apparatus according to claim 1,
   wherein the pulse width limiting circuit limits the pulse width of the driving pulse to be equal to or less than a time obtained by dividing an ET product of the pulse transformer by a voltage value of the driving pulse.

3. The photoacoustic measurement apparatus according to claim 1,
   wherein the discharge control circuit includes a pulse width setting circuit for outputting a pulse signal having a pulse width set in advance and a pulse width control circuit for generating the driving pulse by limiting the pulse width of the pulse signal output from the pulse width setting circuit to be equal to or less than an upper limit pulse width set in advance.

4. The photoacoustic measurement apparatus according to claim 3,
   wherein the discharge control circuit has a logic circuit.

5. The photoacoustic measurement apparatus according to claim 3,
   wherein the pulse width control circuit is configured to change the upper limit pulse width.

6. The photoacoustic measurement apparatus according to claim 1,
   wherein the capacitor is a capacitor bank.

\* \* \* \* \*